(12) United States Patent
Al-Shemmeri

(10) Patent No.: US 9,119,963 B1
(45) Date of Patent: Sep. 1, 2015

(54) ELECTRIC DEVICE FOR PRODUCING SUCCESSIVE POSITIVE AND NEGATIVE ELECTRIC CHARGES

(71) Applicant: Mohammad Ali Al-Shemmeri, Andalous (KW)

(72) Inventor: Mohammad Ali Al-Shemmeri, Andalous (KW)

( * ) Notice: Subject to any disclaimer, the term of this patent is extended or adjusted under 35 U.S.C. 154(b) by 0 days.

(21) Appl. No.: 14/567,931

(22) Filed: Dec. 11, 2014

(51) Int. Cl.
*A61N 1/32* (2006.01)
*A61N 1/36* (2006.01)
*A61N 1/04* (2006.01)
*A61N 1/375* (2006.01)

(52) U.S. Cl.
CPC .......... *A61N 1/36014* (2013.01); *A61N 1/0472* (2013.01); *A61N 1/375* (2013.01)

(58) Field of Classification Search
CPC ..... H03K 3/352; A61N 1/32; A61N 1/36014; A61N 1/36125; A61N 1/375
USPC .................................. 607/61, 76, 2
See application file for complete search history.

(56) References Cited

U.S. PATENT DOCUMENTS

| 1,532,463 | A | 4/1925 | Winterfield |
| 3,640,284 | A | 2/1972 | Langis |
| 4,033,356 | A | 7/1977 | Hara |
| 4,541,432 | A | 9/1985 | Molina-Negro et al. |
| 4,976,263 | A | 12/1990 | Seidl et al. |
| 6,026,327 | A | 2/2000 | Dervieux |
| 6,249,706 | B1 | 6/2001 | Sobota et al. |
| 7,343,203 | B2 * | 3/2008 | Reinhold ........................ 607/63 |
| 2006/0187607 | A1 * | 8/2006 | Mo ............................... 361/143 |
| 2007/0276449 | A1 | 11/2007 | Gunter et al. |

FOREIGN PATENT DOCUMENTS

| CA | 2228717 A1 | 3/1997 |
| WO | WO 9309843 A1 | 5/1993 |

* cited by examiner

*Primary Examiner* — Christopher D Koharski
*Assistant Examiner* — Michael Carey
(74) *Attorney, Agent, or Firm* — Richard C. Litman

(57) ABSTRACT

The electric device for producing successive positive and negative electric charges includes a thyristor-based electrical pulse generator for providing alternating positive and negative pulses with relatively small currents. The potential alternates between positive and negative charge current, and the small current is applied, in the form of sparks, to a body under treatment. A cup-shaped electrode is mounted in the distal end of a handle for application to the body. The treatment device is carried in a case for portability.

2 Claims, 3 Drawing Sheets

US 9,119,963 B1

ELECTRIC DEVICE FOR PRODUCING SUCCESSIVE POSITIVE AND NEGATIVE ELECTRIC CHARGES

BACKGROUND OF THE INVENTION

1. Field of the Invention

The present invention relates to treating bodily disorders and ailments, and particularly to an electric device for producing successive positive and negative electric charges for treating and fostering the healing of bodily disorders.

2. Description of the Related Art

Bio-electric stimulation therapy or electrotherapy is the use of electrical energy as a medical treatment. In medicine, the term electrotherapy can apply to a variety of treatments, including the use of such electrical devices as deep brain stimulators for neurological disease. The term has also been applied specifically to the use of electric current to speed wound healing. Additionally, the term "electrotherapy" or "electromagnetic therapy" has also been applied to a range of alternative medical devices and treatments. Most electrotherapy devices use at least a pair of electrodes attached to the body in order to pass a charge or current through the body. These devices require electrodes to be attached to the body, generally with some sort of conductive adhesive in the form of pads, etc., to be adhered to the body, which become unduly sticky, and can cause harm if not applied properly.

Thus, an electric device for producing successive, positive and negative electric charge pulses solving the aforementioned problems of stickiness, and harmful currents is desired.

SUMMARY OF THE INVENTION

The electric device for producing successive positive and negative electric charges in small amounts to a patient to treat ailments of the body has an electrical pulse generator alternating between positive and negative pulses with relatively small currents. The potential alternates between positive and negative, and the small current is applied, in the form of sparks, to a body under treatment. A cup-shaped electrode is mounted in the distal end of a handle for application to the body. The treatment device is carried in a case for portability.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The electric device for producing successive positive and negative electric charges is a device for the treatment of ailments within the body. The charges typically interact with the positive and negative charged ions in the body, mainly the blood, causing the gathering of these ions in order for the body to naturally address them, thereby promoting the healing of the ailments affecting the body.

Figure 1:
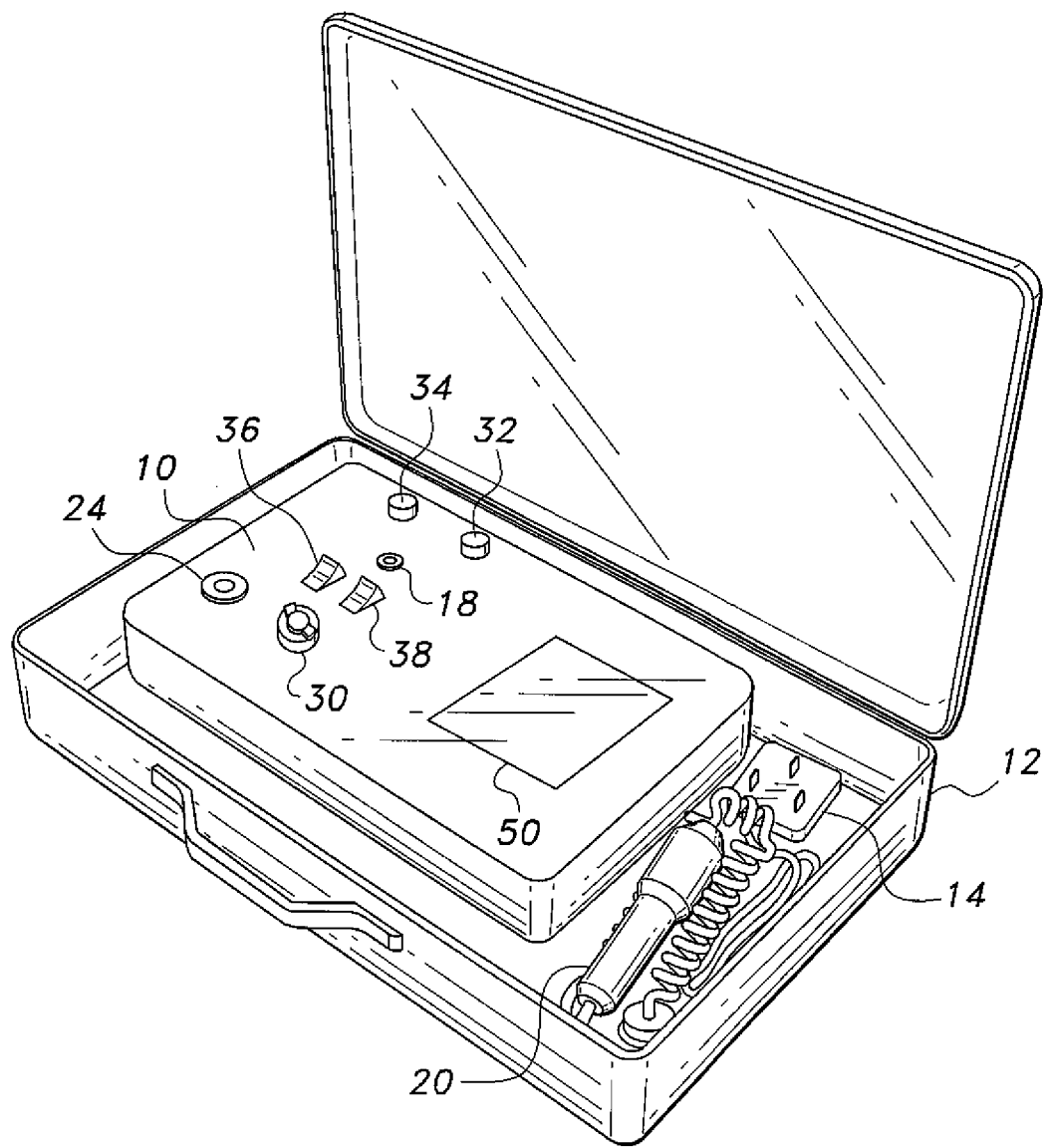
FIG. 1 is an environmental perspective view of an electric device for producing successive positive and negative electric charges according to the present invention, shown packed in a carrying case for transport.

Referring to FIG. 1, the device 10 is compact and portable, whereby it may be transported in a carrying case 12, such as a briefcase or suitcase. The case 12 assures that the practitioner has the unit available at a moment's notice if a patient is requiring treatment immediately. Within the case 12 are the device 10 that produces the successive, positive and negative electric charges, the power supply plug 14 and cord 16, and the administering handheld unit 20 and cable 22.

Figure 2:
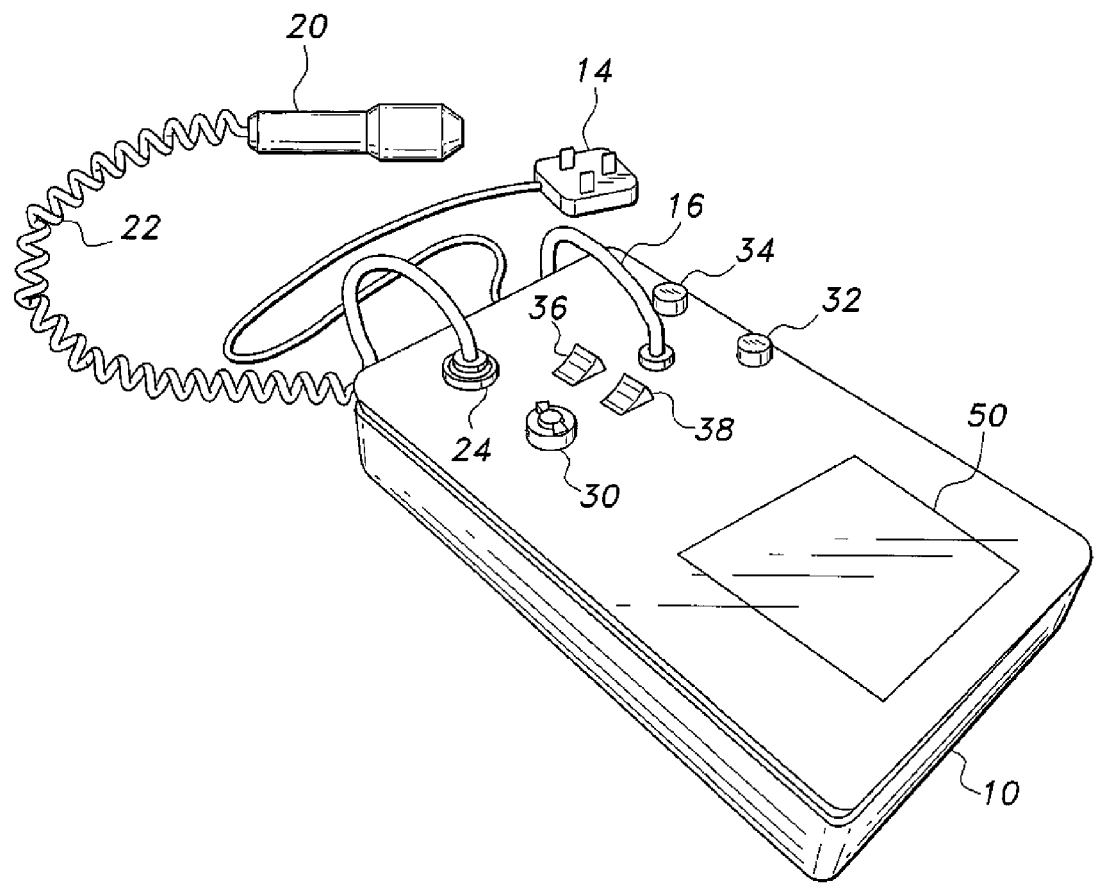
FIG. 2 is a perspective view of the electric device for producing successive positive and negative electric charges according to the present invention.

The device 10 includes a label 50 carrying indicia describing the operational use of, safety precautions, and warnings for the unit. As seen in FIGS. 1 and 2, the device 10 has connector 18 for the cord 16 of the power supply plug 14. The end of the cord 16 connects to the internal circuitry of the device 10 via the connector 18. An ON/OFF switch 36 is electrically connected internally of the device 10 to the cord 16. The ON/OFF switch 36 is selectively used to provide power to the device 10 via power supply plug 14 and cord 16. Also, a fuse 32 is provided for preventing any undue currents or voltages received from an ordinary outlet to damage the device 10.

The handheld unit 20 is connected to the device 10 via cord 22. The end of cord 22 connects to connector 24 of device 10. Also, another fuse 34 is electrically connected to the connector 24 for protecting the patient receiving treatments from being inadvertently shocked via any current or voltage surge from a power source via the power supply plug 14 and cord 16. In addition, an output control knob 30 is provided on the device 10 for regulating the intensity of the pulses presented to the patient at the handheld unit 20. The device 10 has a circuit for generating successive positive and negative electrical pulses. The amplitude or intensity of the generated pulses is controlled by the knob 36. The device 10 uses a thyristor-based pulse generator circuit, which are well known in the art. Such circuits are described in Canadian patent number CA 2228717, published March 1997, and in U.S. Pat. No. 7,343,203, issued to Reinhold, both of which are hereby incorporated by reference in their entirety. The device 10 includes a transducer in the form of the handheld unit 20, which conveys the alternating pulses to the person in need of treatment.

Figure 3:
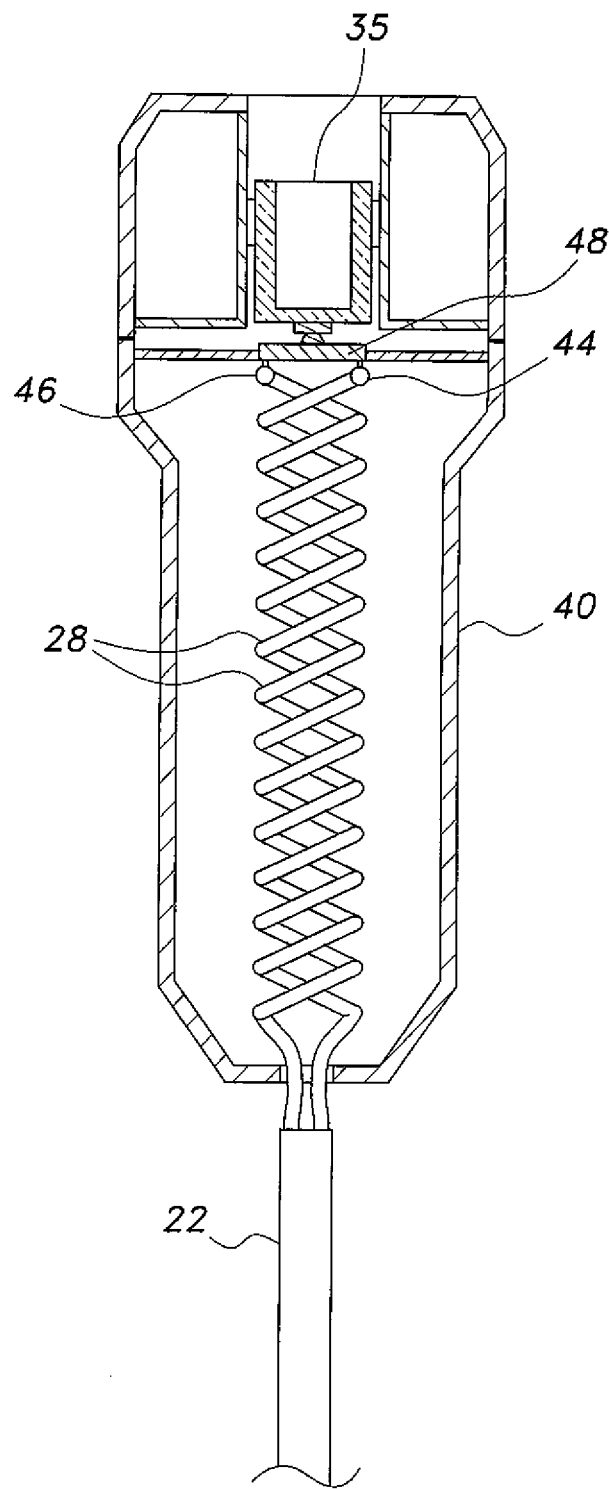
FIG. 3 is a side view in section of the handle of the electric device for producing successive positive and negative electric charges according to the present invention.

Referring to FIG. 3, the details of the handheld unit are described via the cross-sectioned illustration. The handheld unit has an insulated, ergonomic handle 40. The handle 40 holds a conductive cup 35 at a distal end. The conductive cup 35 may be formed from copper, or another suitable conductive medium. The cup releases the successive, positive and negative electric charges to the patient when the distal end is placed adjacent to the skin surface of the patient. The conductive cup 35 is coupled to a connector plate 48. The connector plate 48 transfers the successive positive and negative electric charges from a pair of helically coiled copper electrodes forming a coil 28 inside the insulated handle 40.

The cord 22 from the device 10 terminates at the electrode pair 28 within the handheld unit 20. The purpose of the electrode pair in the coil 28 is to provide a self-balancing of the generated pulses as they are delivered to the patient. The ends of the coil wire pair 28, opposite the cord 22, are separately connected to the connector plate 48 at contact points 44 and 46. The contact points 44 and 46, due to the application of the successive positive and negative electric charges from the device 10 via the cord 22 to the handheld unit 20, provide a charge-coupling effect to the conductive cup 42. This function thereby delivers the charges to the conductive cup 42, which thereby attracts the ions of the patient when the cup 42 is in close proximity to the skin surface of the patient.

It is to be understood that the present invention is not limited to the embodiments described above, but encompasses any and all embodiments within the scope of the following claims.

I claim:

1. An electric device for producing successive positive and negative electric charges, comprising:
    a thyristor-based pulse generator circuit for generating a plurality of successive positive and negative electrical pulses;
    a handheld transducer connected to the pulse generator circuit, the handheld transducer having a distal end, the transducer delivering the generated plurality of successive positive and negative pulses to the distal end;
    wherein, when handheld unit is brought into contact with a patient at a localized area to be treated, the plurality of successive positive and negative charge pulses are delivered to the patient;
    a conductive cup in the distal end of said handheld transducer, the conductive cup delivering the plurality of successive positive and negative charge pulses;
    a coil electrically connected to the conductive cup and the pulse generator circuit, the coil being disposed within the handheld electrotherapeutic device; and
    insulation surrounding the cup and the coil.

2. The electric device according to claim 1, further comprising:
    a carrying case for storing and transporting the handheld unit transducer and said pulse generator circuit; and
    means for providing electrical power to said circuit.

* * * * *